(12) United States Patent
D'Costa et al.

(10) Patent No.: US 8,927,918 B2
(45) Date of Patent: Jan. 6, 2015

(54) OPTICAL SENSOR ELEMENT AND OPTICAL SAMPLE ANALYZING APPARATUS

(75) Inventors: Eric D'Costa, Wotton-under-Edge (GB); Sunny Bhachoo, Brockworth (GB); John Eveness, Bristol (GB); Teresa Joe, Hawera (NZ)

(73) Assignee: ABB Technology AG, Zürich (CH)

( * ) Notice: Subject to any disclaimer, the term of this patent is extended or adjusted under 35 U.S.C. 154(b) by 149 days.

(21) Appl. No.: 13/367,810

(22) Filed: Feb. 7, 2012

(65) Prior Publication Data
US 2012/0312973 A1 Dec. 13, 2012

(30) Foreign Application Priority Data

Feb. 9, 2011 (EP) .................................. 11001038

(51) Int. Cl.
*G01N 21/53* (2006.01)
*G01N 21/15* (2006.01)

(52) U.S. Cl.
CPC ................ *G01N 21/53* (2013.01); *G01N 21/15* (2013.01); *G01N 2201/0238* (2013.01)

USPC ......................................................... 250/216

(58) Field of Classification Search
USPC ......................................................... 250/216
See application file for complete search history.

(56) References Cited

U.S. PATENT DOCUMENTS 5,446,544 A * 8/1995 Beers ............................ 356/339

FOREIGN PATENT DOCUMENTS

WO    WO 2010/059176 A1    5/2010

* cited by examiner

*Primary Examiner* — Tony Ko
(74) *Attorney, Agent, or Firm* — Buchanan, Ingersoll & Rooney PC (57) ABSTRACT

An exemplary optical sensor element for use in an optical sample analyzing apparatus, includes a housing that includes at least one optical sensor component. A housing body and a housing lid are removably connected to the housing body so that in an assembled state, the housing body and the housing lid form a fluid-tight housing. The housing lid is equipped with replaceable moisture control elements.

11 Claims, 5 Drawing Sheets

OPTICAL SENSOR ELEMENT AND OPTICAL SAMPLE ANALYZING APPARATUS

RELATED APPLICATION

This application claims priority under 35 U.S.C. §119 to European Patent Application No. 11 001 038.6 filed in Europe on Feb. 9, 2011, the entire content of which is hereby incorporated by reference in its entirety.

FIELD

The disclosure relates to an optical sensor such as an optical sensor element for use in an optical sample analyzing apparatus, wherein the optical sensor element is configured as light emitting element, and another optical sensor element is configured as light receiving element.

BACKGROUND

Known optical sensor elements used in an optical sample analyzing apparatus are described in WO 2010/059176 A1. This document discloses a nephelometric turbidity meter as an example for an optical sample analyzing apparatus. Another nephelometric turbidity meter as an example for an optical sample analyzing apparatus is shown in U.S. Pat. No. 5,446,544.

Known optical sensor elements can include an optical window to provide the optical interface to the sample to be analyzed. Samples to be analyzed may be liquids or gases. In known optical sample analyzing apparatuses, the sample to be analyzed is a liquid, the analyzing method is nephelometric turbidity measurement.

One of the challenges when applying an optical sensor element in an optical analyzer apparatus is moisture build-up and fogging on the inside surface of the optical sensor element due to differences in fluid temperature outside the optical window from internal air temperature on the interior side of the optical window.

In WO 2010/059176 A1 the problem of moisture buildup and fogging is addressed by applying a multiple, sealed window construction for the optical window. This, however, is complicated and expensive from a manufacturing point of view and is not service-friendly. For example, in instances when fogging still occurs, the whole optical sensor element has to be exchanged.

In U.S. Pat. No. 5,446,544 the problem of moisture buildup and fogging is addressed by equipping the optical sample analyzing apparatus with a tray filled with a desiccant dryer material, which is meant to reduce the moisture in the internal atmosphere in the analyzing apparatus. This solution, however, is complicated and expensive as well and not service-friendly, because when the desiccant is saturated, the whole apparatus has to be disintegrated to exchange the desiccant, or one would apply a large amount of desiccant material, which makes the apparatus voluminous and expensive.

SUMMARY

An exemplary optical sensor element for use in an optical sample analyzing apparatus is disclosed, comprising: a housing that includes at least one optical sensor component and an optical window, wherein the housing is equipped with window heating means arranged near the optical window.

An exemplary optical sample analyzing apparatus is disclosed, comprising: a housing that includes at least one optical sensor component and an optical window; and a light measuring device electrically connected to an electronic circuitry, wherein the housing is equipped with window heating means arranged near the optical window, and wherein the optical sensor element is a light receiving element.

An exemplary optical sample analyzing apparatus configured to work as a modular nephelometric turbidity sensor device is disclosed, comprising: a measuring cell body, to which are coupled a sample feed/drain unit; a housing that includes at least one optical sensor component and an optical window; a light measuring device electrically connected to an electronic circuitry; and a terminal box, wherein the housing is equipped with window heating means arranged near the optical window, and wherein the optical sensor element is a light receiving element.

BRIEF DESCRIPTION OF THE DRAWINGS

The disclosure will be described in greater detail by description of an embodiment with reference to the accompanying drawings, wherein.

DETAILED DESCRIPTION

Exemplary embodiments of the present disclosure provide an optical sensor element for use in an optical sample analyzing apparatus that avoids moisture buildup and fogging on the inside surface of the optical sensor element in a simple, low-cost and service-friendly manner.

Exemplary embodiments of the present disclosure also provide an optical sample analyzing apparatus with at least one optical sensor element configured as light emitting element, and with at least another optical sensor element configured as light receiving element that avoids moisture buildup and fogging on the inside surfaces of the optical sensor elements in a simple, low-cost and service-friendly manner.

According to the present disclosure an exemplary housing is equipped with window heating means arranged near the optical window. A heater component is placed in close proximity to the sample window in the housing of the optical sensor element. The heater is used to prevent or dissipate the build up of condensation on the inside surface of the optical window that may arise as a result of moisture ingress in the sensor element housing over time. This feature will facilitate uninterrupted measurements under conditions where internal condensation could cause the optical sensor element to fail.

Another advantageous aspect of the exemplary housing further includes a housing body and a housing lid, which is removably connected to the housing body, so that in the assembled state the housing body and the housing lid are forming a fluid-tight housing, and wherein the housing lid is equipped with replaceable moisture control elements.

In yet another advantageous aspect of the present disclosure an exemplary moisture control element includes a piece of moisture absorbent material, or desiccant dryer material, included in a replaceable capsule. The housing lid is equipped with capsule retention features, or support means for the moisture absorbent materials, which support means removably hold the capsules. Thus the moisture absorbent material will absorb moisture in the interior of the optical sensor element. When the absorbent material is saturated and does not absorb any further moisture, it can be easily replaced, in such a way that the operator replaces the housing lid with the used capsules by a new housing lid with new capsules. The operator not even has to change the individual caps. A housing lid, loaded with fresh moisture absorbent capsules, can be held on stock as a spare part and easily be replaced, without affecting the rest of the sensor element, without a need for further disassembly with cumbersome reassembly of the sensor element. This facilitates the simple replacement of moisture control material in the field by non-skilled users. Because the replacement is so easy, it could be done even with a somewhat higher frequency, if the amount of moisture absorbing material per load in one housing lid is relatively small. Of course, the non-skilled user could as easily also replace the individual capsules of moisture absorbing material, which would save the material cost for replacing the whole housing lid. Alternatively, one could also reuse an exchanged housing lid by replacing the capsules in the old lid and installing this refurbished lid in the next service cycle.

An advantageous aspect of the present disclosure provides an exemplary optical window for having an optical path from the optical sensor component to the sample is included in the housing body, and the window heating means arranged near the optical window are located in the housing body.

In an exemplary embodiment of the present disclosure the optical sensor component includes a lens holder with an optical lens facing the optical window, and with an optical aperture on the side opposite the optical lens. The lens holder may be fixed to the housing body. It supports the collimator lens assembly in the optical path. The lens holder advantageously includes the optical compounds necessary to realise the optical path from the optical window on the sample side to a light source in case the optical sensor element is a light emitting element, or from the optical window to a light receiving element in case the optical sensor element is a light receiving element. By installing the lens holder as a separate subunit including the optical path, the basis is laid for a modular design of the optical sensor element either as a light receiving or a light emitting element. For both applications the housing body, the housing lid and the lens holder can remain widely unchanged, and the difference in application can be achieved by exchanging a further component, either a light source or a light receiving element, that can easily be connected to the lens holder.

An exemplary optical sensor element of the present disclosure is a light receiving element and the optical sensor component further comprises a light measuring device electrically connected to an electronic circuitry. The light measuring device may be a photodiode, which is placed at the optical aperture of the lens holder, so that the light coming from the optical window through the optical path provided by the lens holder is directed directly to the photodiode. In another exemplary embodiment, the photodiode can be mounted on a printed circuit board (PCB), the PCB carrying the electronic circuitry for evaluating the received light and further processing of the sensor signal. So the subunit of PCB and photodiode can in a modular way be inserted into the housing of the optical sensor element to adapt it to become a light receiving element.

According to an advantageous aspect of the present disclosure, an exemplary optical sensor element is a light emitting element, and the optical sensor component further includes a light source included in a light source holder, the light source holder having a second optical aperture to route light from the light source out of the light source holder into the optical aperture of the lamp holder. In another exemplary embodiment, the light source holder is removably connected to the lens holder to form a modular light emitting unit, wherein the second optical aperture of the light source holder is aligned with the optical aperture of the lens holder. The lamp holder thus locates a light source in a reproducible aligned position in the optical train of the collimator assembly. It facilitates the reproducible positioning of the light source in the optical train. The lamp holder facilitates replacement of the light source in the field by nonskilled users. It allows users to replace an expired light source without handling critical optical surfaces, and without touching of the light emitting devices. The lamp holder can be used with all kinds of light emitting devices, for example either with an NIR LED or an incandescent tungsten filament lamp. The configuration enables a modular design of the lamp holder and the lens holder to be assembled into a modular optical sensor component.

In an exemplary embodiment disclosed herein, the light source holder includes a light pipe integrally formed to the light source holder, for routing an additional portion of the light from the light source out of the light source holder on a further path. An exemplary optical sensor element can include a reference light measuring device coupled to a feedback control circuit configured to control the light output of the light source.

Both the lamp holder and the light pipe, in a further exemplary embodiment of the disclosure can be made of a transparent material, such as for example, but not exclusively, a transparent plastic material. The light pipe and the body of the lamp holder may in this case be produced integrally in one step, e.g. by injection moulding.

The exemplary lamp holder with the integrally formed light pipe provides routing of a portion of light via the integral light guide onto a reference photodiode to control the light output of the lamp using a feedback control circuit. The lamp holder with integrated light pipe is thus guiding and concentrating light from the analytical light source onto a photodiode or other light-sensitive area for feedback control of the light source.

According to a further advantageous aspect of the present disclosure an exemplary light source holder includes a detent mechanism for removably fixing the light source holder to the lens holder. The detent mechanism for secure fixing into the lens holder/collimator may in an advantageous embodiment be using integral deformable ergonomic finger pinch handles, which may be designed in the form of resilient arms.

An exemplary optical sample analyzing apparatus, according to the present disclosure can be equipped with at least one optical sensor element as described above being configured as a light receiving element, and with at least one optical sensor element as described above being configured as a light emitting element.

In another exemplary embodiment, the optical sample analyzing apparatus, according to the present disclosure, is configured to work as a modular nephelometric turbidity sensor device, a measuring cell body, to which are coupled a sample feed/drainunit, the optical sensor element as described above being configured as a light receiving element, the optical sensor element as described above being configured as a light emitting element, and a terminal box.

In a further exemplary embodiment of the present disclosure there is coupled to the measuring cell body a cleaner module for automatically cleaning the optical windows in contact with the sample.

Figure 1A:
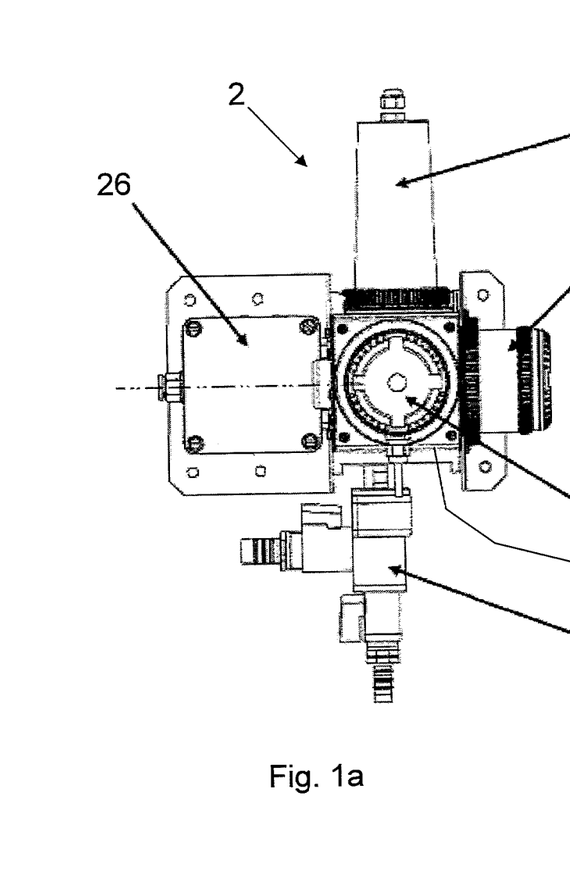
FIG. 1a shows an embodiment of an optical sample analyzing apparatus in a front view in accordance with an exemplary embodiment.
Figure 1B:
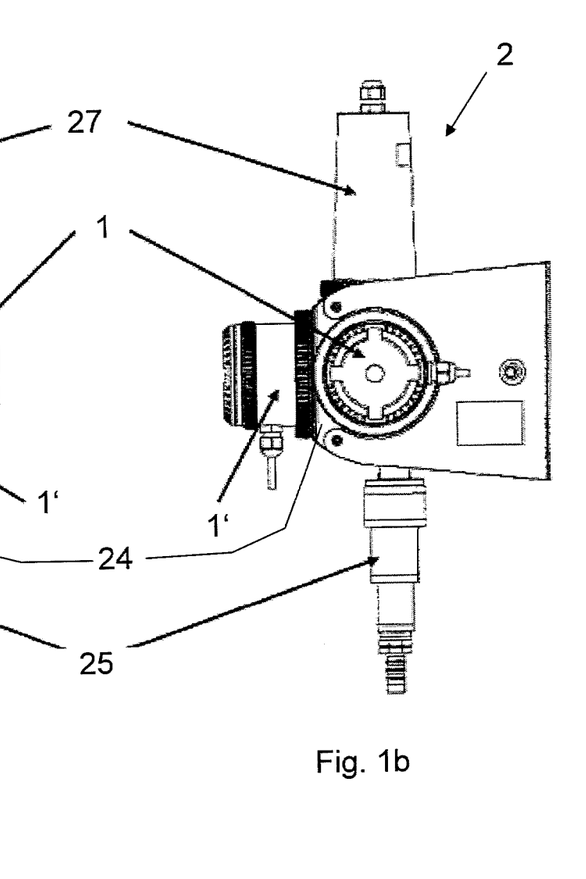
FIG. 1b shows the embodiment of an optical sample analyzing apparatus of FIG. 1a in a left side view in accordance with an exemplary embodiment.

FIG. 1a shows an embodiment of an optical sample analyzing apparatus in a front view in accordance with an exemplary embodiment. FIG. 1b shows the embodiment of an optical sample analyzing apparatus of FIG. 1a in a left side view in accordance with an exemplary embodiment. In particular, FIGS. 1a and 1b show a front view and a side view of a modular nephelometric turbidity sensor device 2 in accordance with an exemplary embodiment. Central unit is a measuring cell 24, and sample liquid is fed to the measuring cell 24 and removed from it via a feed/drain unit 25 which is removably coupled to the measuring cell 24 with a piping coupling mechanism. Further attached to the measuring cell body 24 are a first optical sensor element 1, which is configured as a light emitting device, and a second optical sensor element 1', which is configured as a light receiving element. Both optical sensor elements 1, 1' are mounted at an angle of 90°, as is known when the nephelometric turbidity sensing principle is applied.

Additionally, there is coupled to the measuring cell 24 a cleaner module 27 and a terminal box 26.

Nephelometry is an optical turbidity sensing method evaluating the light scattered by the particles in the fluid at an angle of 90° in respect to an incident light beam.

There are worldwide standard specifications for the measurement of turbidity in water treatment. The USEPA 180.1 Nephelometric Method, 2130B Standard Methods for the Examination of Water and Waste Water and the ISO 7027 International Standard Water Quality Determination of Turbidity 19991215, Hach 10133, GLI Method II, Mitchell Method M5331 LED, and Mitchell Method M5271 laser. All specifications measure the intensity of scattered light from suspended particles in the fluid having a refractive index different from that of the sample fluid, measured at a 90 degree angle to the path of the incident light. In order to satisfy the various wavelengths specified by different government agencies, a number of light sources have been EPA approved for nephelometric turbidity measurement and reporting: USEPA 180.11 Incandescent 22003000K tungsten wire, USEPA 180.12 LED 860 nm GLI 4beam, USEPA 180.13 LED 660 nm photomultiplier tube, USEPA 180.14 LED 525 nm Mitchell Method M5331, USEPA 180.15 Laser 660 nm Mitchell Method M5271, ISO 7027 basic LED 860 nm International, ISO 7027 alternate LED 550 nm International.

Figure 2A:
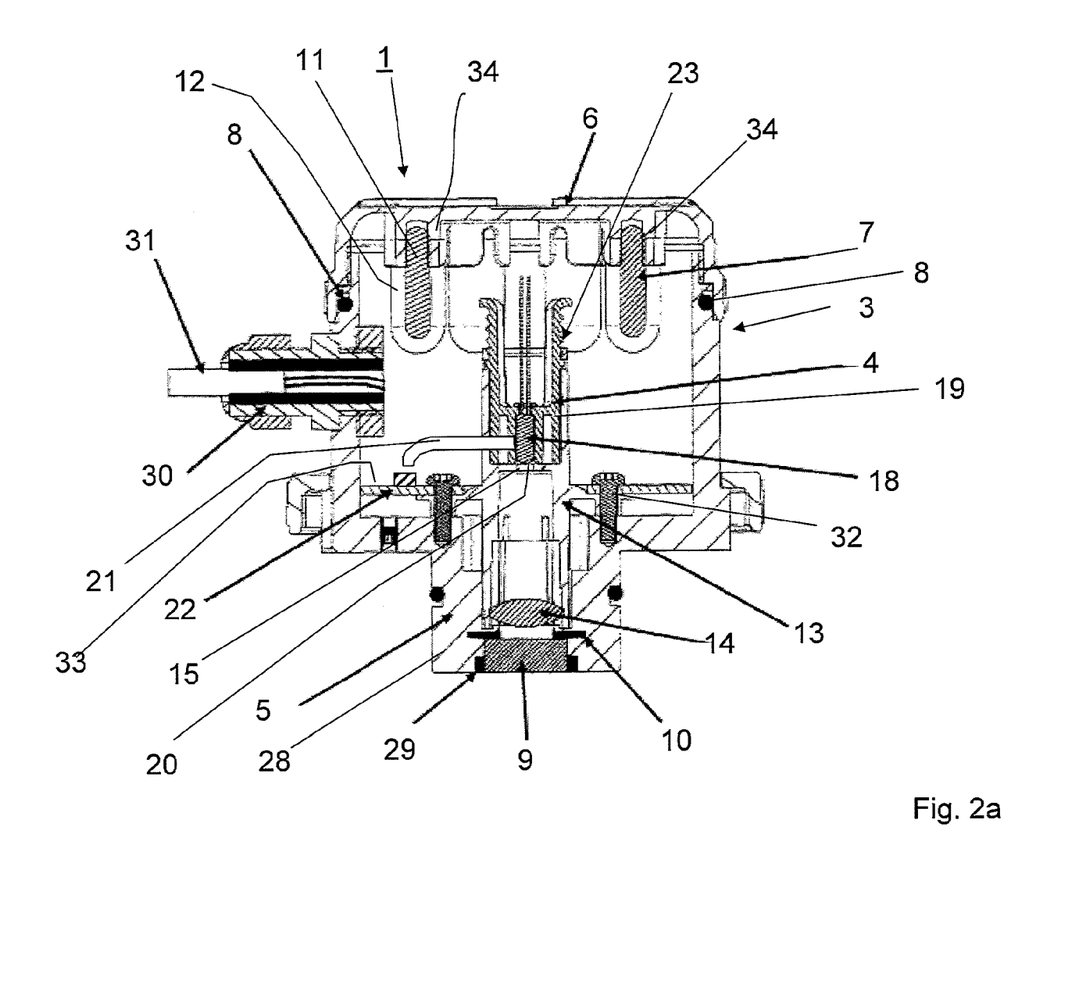
FIG. 2a shows an optical sensor element configured as a light emitting device in accordance with an exemplary embodiment.

FIG. 2a shows an optical sensor element configured as a light emitting device in accordance with an exemplary embodiment. The sensor element 1 has a housing body 5 and a housing lid 6, both with threaded ends so that they can be assembled and screwed together, having first sealing means 8, e.g. an elastic O-ring, in between to form a water and light-tight housing 3. The housing body 5 has a leg-like attachment 28, which has a flat end side which is covered by an optical window 9 fixed to the housing body with a window seal 29. Near the optical window 9 there is a window heating means 10. e.g. in form of an electric heater coil. Attached to the side face of the housing body there is a cable gland 30 giving water and light-tight access of an electric cable 31 to the interior of the housing 3. The cable 31 provides power and signal connection between the optical sensor element 1 and the terminal box 26. The cable 31 is shown only in its part within the cable gland 30.

Inserted into the housing body 5 is an optical sensor component 4, which is in a modular way composed of a lens holder 13 and a light source holder 19, which are both detachably kept together by a detent mechanism 23 comprising two resilient detent levers, comprising integral deformable ergonomic finger/thumb pinchhandles.

The lens holder 13 is fixed to the housing body with screws 32, which simultaneously also fix a printed circuit board (PCB) 33 to the housing body. The PCB has on it an electronic circuitry and attached to it a reference light measuring device 22.

The lens holder provides a collimated optical path, between an optical lens 14 on the side facing the optical window 9 and an optical aperture 15 on the opposite side.

The light source holder 19 is made of a transparent plastic material. It holds a light source 18, which can be either a LED, a laser diode or a tungsten wire lamp, and has a second optical aperture 20 which in assembled position lies adjacent to the optical aperture 15 of the lens holder 13 and permits the main part of the light from the light source 18 to pass into the optical path and leave the housing 3 through the optical window 9 in a focused way.

Integral with the light source holder there is a light pipe 21, in the form of a transparent arm, leading a part of the light from the light source 18 sideways and directing it to the reference photodiode 22, which is used to control the light output of the light source 18 using a feedback control circuit being part of the electronic circuitry on the PCB.

On the inner side of the upper part of the housing lid 6 there are holding fixtures 34 integrally formed in the lid wall, which removable hold and support moisture control elements 7. Each moisture control element 7 is a capsule 12 filled with moisture absorbent material 11. If the moisture control elements need to be replaced, one opens the housing lid 6 and either replaces each of the capsules 12 individually, or one fixes a new lid with fresh capsules to the housing body.

In case the light source 18 needs to be replaced, one opens the lid 6 and detaches the light source holder 19. This can easily be done by compressing manually the two resilient arms of the detent mechanism, which will set free the lamp holder 19 so that it can easily be withdrawn from the lens holder 13. A new lamp holder with a new light source is inserted just the same way back. It is not necessary to touch the light source. Alignment with the optical path and alignment of the light pipe 21 with the reference photodiode is achieved automatically through the guidance given by the lens holder 13 to the lamp holder 19. Exchanging the lamp is thus achievable by a simple plugin action that can be done also by unskilled users. As easy is it to change the type of lamp, by just plugging in a lamp holder equipped with the new type of lamp.

Figure 2B:
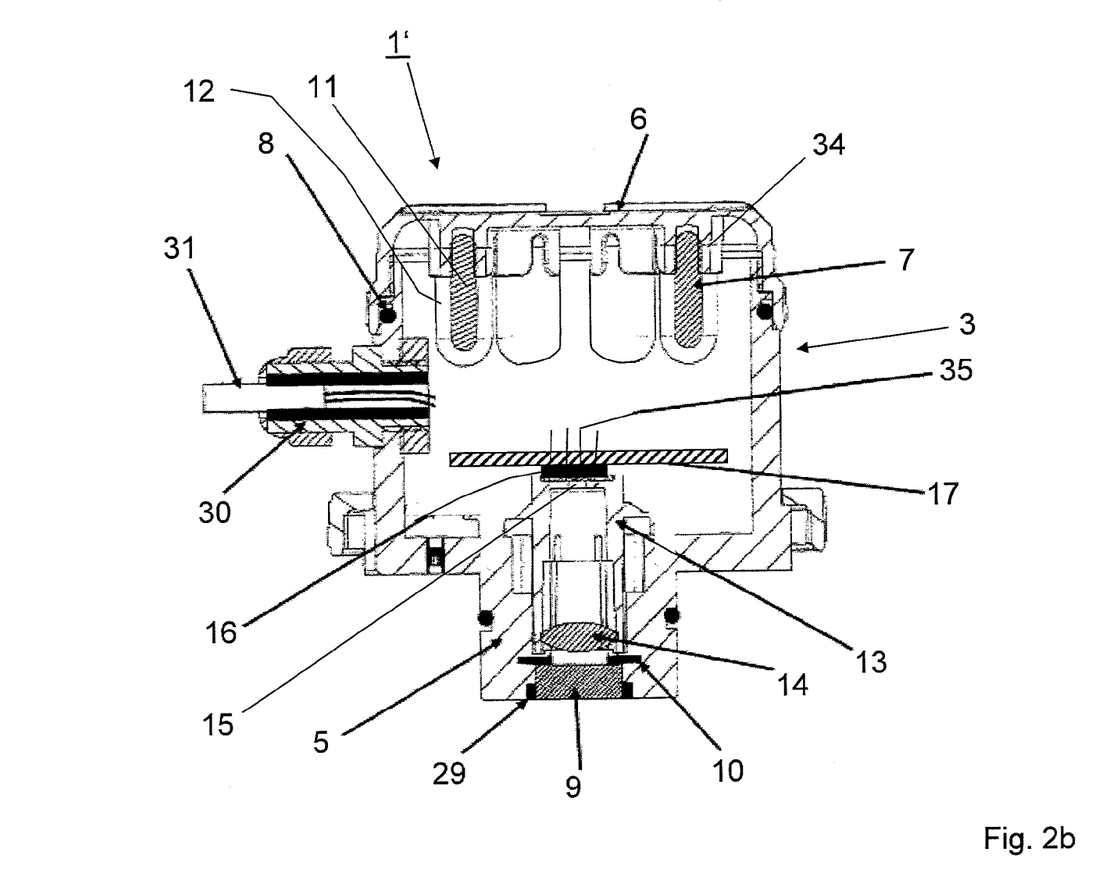
FIG. 2b shows an optical sensor element configured as a light receiving device in accordance with an exemplary embodiment.

FIG. 2b shows an optical sensor element configured as a light receiving device in accordance with an exemplary embodiment. The optical sensor of FIG. 2b is substantially identical to the embodiment of the light emitting device described in FIG. 2a, except that there is no lamp holder any more and the PCB 33 has been removed. Instead, a light measuring device 16, for example a photodiode, is mounted close to the optical aperture 15 of the lens holder 13. The photodiode 16 is mounted to an electronic circuitry 17, again in form of a PCB, via contact pins 35. The other parts or elements having the same reference numerals in both FIGS. 2a and 2b are identical in function.

One can see, that by the modular design according to the disclosure it is easily possible to interchange the light emitting and light receiving modules in an optical measurement sample analyzing apparatus like a nephelometric turbidity sensor.

Figures 3A, 3B, 3C:
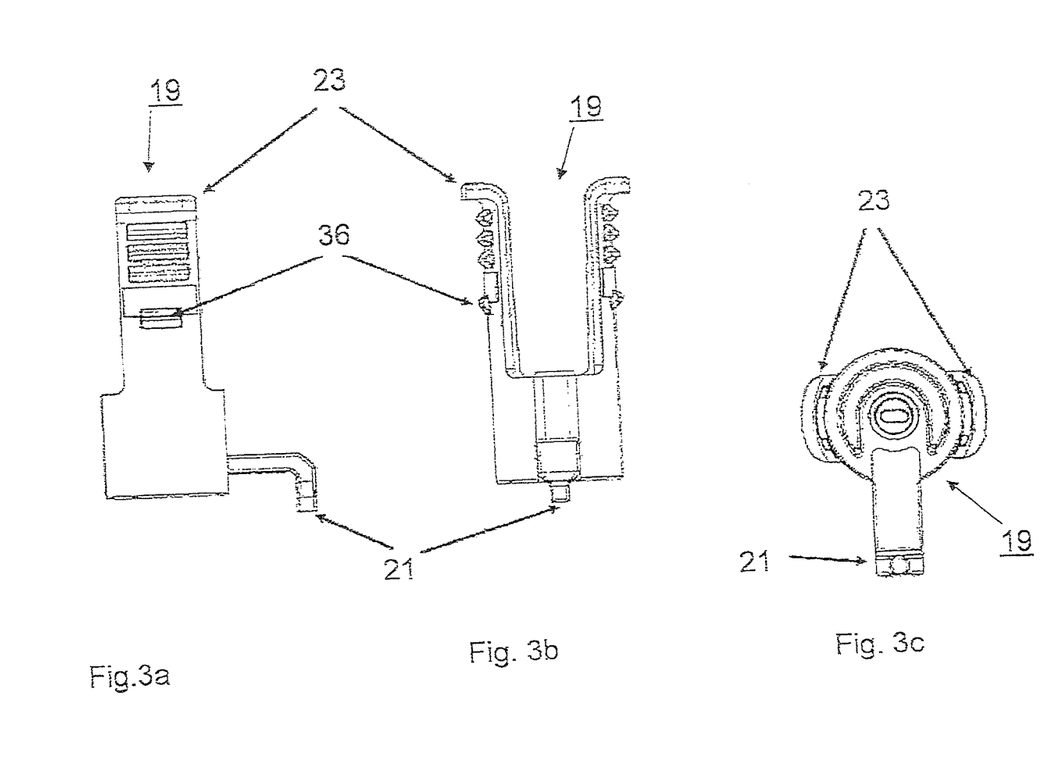
FIG. 3a shows a side view of a lamp holder in accordance with an exemplary embodiment.
FIG. 3b shows a front view of a lamp holder according to FIG. 1a in accordance with an exemplary embodiment.
FIG. 3c shows an underside view of a lamp holder according to FIG. 1a in accordance with an exemplary embodiment.

FIGS. 3a, b and c show a detailed view of the lamp holder 19, in side view (FIG. 3a), front view (FIG. 3b) and underside view (FIG. 3c) in accordance with an exemplary embodiment. The lamp holder 19 has already been described in detail above. In each Figure one can see in greater detail the deformable ergonomic design of the finger/thumb pinch handles that are realised in the form of resilient arms with tooth-like bumps on the outside of the arms. One can also see a notching tooth 36 that serves as part of the detent mechanism and interacts with a corresponding notching cutout in the lens holder to removably hold the lamp holder in the lens holder.

Figure 4A:
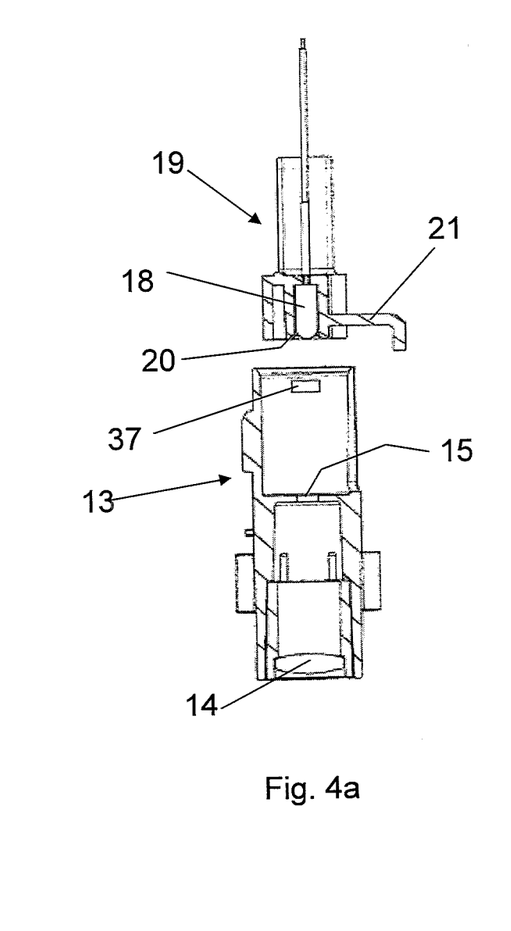
FIG. 4a shows a lamp holder and a light source before assembly in accordance with an exemplary embodiment.
Figure 4B:
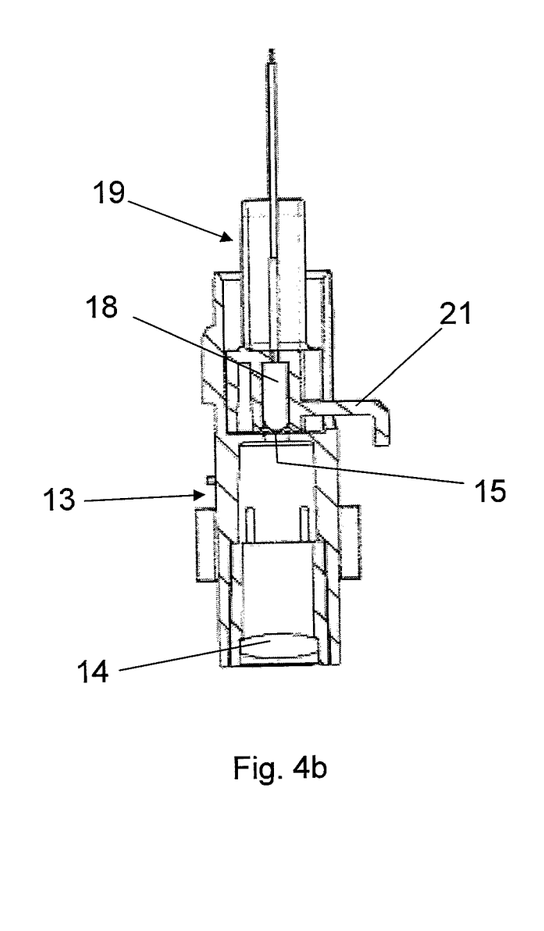
FIG. 4b shows an ensemble of a lamp holder and a light source according to FIG. 4a after assembly in accordance with an exemplary embodiment.

FIG. 4a shows a lamp holder and a light source before assembly in accordance with an exemplary embodiment. FIG. 4b shows an ensemble of a lamp holder and a light source according to FIG. 4a after assembly in accordance with an exemplary embodiment. FIGS. 4a and 4b demonstrate the simple manual insertion procedure of the lamp holder 19 to the lens holder 13 to the positive detent location using the deformable, resilient pinch handles of the lamp holder 19. One sees the notching cutout 37 in the lens holder 13 that will detent the lamp holder 19 in its position for correct optical alignment and collimation with the lens holder 13. In the side walls of the lens holder, at the outer surface area, there are slots provided oriented in axial direction. Their purpose is to serve as channels for moist air driven off the heated window 9 (see FIG. 2a), so that an improved air flow out of the window area is achieved and further supports the antifogging effect of the window heater.

To shortly summarise, the advantages and advantageous effects achieved with an exemplary optical sensor element according to the present disclosure includes improved moisture handling capability, an integral sample window heater for prevention of condensation, user-replaceable light sources by easy plugin, user-replaceable desiccant capsules, independent light emitting and light receiving pairs.

The present disclosure was widely described in relation to the application of exemplary optical sensor elements 1, 1' in a nephelometric turbidity sensor apparatus. However, it should be understood that the concept of modular design of the optical sensor element 1, 1' is not limited to this specific application. The beneficial effect of the disclosure in respect of improvement to light control and moisture control in optical sensors can also apply widely to other optical analytical sensing systems and apparatuses, such as for example, but not limited to, absorption type of measurement like absorption type of turbidimeter, colorimeter and absorption spectroscopy.

Thus, it will be appreciated by those skilled in the art that the present embodiments can be in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

LIST OF REFERENCE SIGNS

1 Optical sensor element
2 Optical sample analyzing apparatus
3 housing
4 optical sensor component
5 housing body
6 housing lid
7 moisture control element
8 first sealing means
9 optical window
10 window heating means
11 moisture absorbent material
12 capsule
13 lens holder
14 optical lens
15 optical aperture
16 light measuring device
17 electronic circuitry
18 light source
19 light source holder
20 second optical aperture
21 light pipe
22 reference light measuring device
23 detent mechanism
24 measuring cell
25 feed/drain-unit
26 terminal box
27 cleaner module
28 leg-like attachment
29 window seal
30 cable-gland
31 cable
32 screw
33 PCB
34 holding fixture
35 contact pin
36 notching nose
37 notching cut-out

What is claimed is:

1. An optical sensor element for use in an optical sample analyzing apparatus, comprising:
 a housing that includes at least one optical sensor component and an optical window;
 a lens holder with an optical lens facing the optical window, and with an optical aperture on a side opposite the optical lens; and
 a light source included in a light source holder, the light source holder having a second optical aperture to route light from the light source out of the light source holder,
 wherein the housing is equipped with window heating means arranged near the optical window, and
 wherein the light source holder is removably connected to the lens holder to form a modular light emitting unit, wherein the second optical aperture of the light source holder is aligned with the optical aperture of the lens holder.

2. The optical sensor element according to claim 1, wherein the housing further comprises:
 a housing body and a housing lid, wherein the housing lid is removably connected to the housing body, so that in an assembled state, the housing body and the housing lid form a fluidtight housing, and wherein the housing lid is equipped with replaceable moisture control elements.

3. The optical sensor element according to claim 2, wherein the moisture control element comprises a piece of moisture absorbent material included in a replaceable capsule.

4. The optical sensor element according to claim 2, wherein the housing lid is equipped with support means for replaceably holding the moisture control elements.

5. The optical sensor element according to claim 1, wherein the optical window provides an optical path from the optical sensor component to the sample.

6. The optical sensor element according to claim 1, wherein the optical sensor element is a light receiving element, the optical sensor component further comprising:
   a light measuring device electrically connected to an electronic circuitry.

7. The optical sensor element according to claim 1, wherein the light source holder comprises a light pipe integrally formed to the light source holder, for routing an additional portion of light from the light source out of the light source holder on a further path.

8. The optical sensor element according to claim 7, wherein the optical sensor element further comprises a reference light measuring device coupled to a feedback control circuit configured to control the light output of the light source.

9. The optical sensor element according to claim 1, wherein the light source holder comprises a detent mechanism for removably fixing the light source holder to the lens holder.

10. An optical sample analyzing apparatus configured to work as a modular nephelometric turbidity sensor device comprising:
   a measuring cell body, to which are coupled a sample feed/drain unit;
   a housing that includes at least one optical sensor component and an optical window;
   a light measuring device electrically connected to an electronic circuitry; and
   a terminal box,
   wherein the housing is equipped with window heating means arranged near the optical window, and
   wherein the optical sensor element is a light receiving element.

11. The optical sample analyzing apparatus according to claim 10, wherein to the measuring cell body there is coupled a cleaner module for automatically cleaning the optical windows in contact with the sample.

* * * * *